US012642834B2

(12) United States Patent      (10) Patent No.:    US 12,642,834 B2

Schirle et al.            (45) Date of Patent:      Jun. 2, 2026

---

(54) TOPICAL SKIN CARE COMPOSITIONS

(71) Applicant: SkinKick, LLC, Carrollton, TX (US)

(72) Inventors: Matthew Schirle, Mansfield, TX (US); David William Provance, Rio de Janeiro (BR)

(73) Assignee: M and J Properties Joint Venture, Dallas, TX (US)

( * ) Notice: Subject to any disclaimer, the term of this patent is extended or adjusted under 35 U.S.C. 154(b) by 23 days.

(21) Appl. No.: 16/959,634

(22) PCT Filed: Jan. 2, 2019

(86) PCT No.: PCT/US2019/012106
§ 371 (c)(1),
(2) Date: Jul. 1, 2020

(87) PCT Pub. No.: WO2019/136105
PCT Pub. Date: Jul. 11, 2019

(65) Prior Publication Data
US 2020/0384055 A1     Dec. 10, 2020

Related U.S. Application Data

(60) Provisional application No. 62/612,940, filed on Jan. 2, 2018.

(51) Int. Cl.
*A61K 36/76*       (2006.01)
*A61K 9/00*        (2006.01)
           (Continued)

(52) U.S. Cl.
CPC ............ *A61K 36/76* (2013.01); *A61K 9/0014* (2013.01); *A61K 36/47* (2013.01); *A61K 36/48* (2013.01);
           (Continued)

(58) Field of Classification Search
None
See application file for complete search history.

(56) References Cited

U.S. PATENT DOCUMENTS

| | | | | | |
|---|---|---|---|---|---|
| 8,545,904 | B1 * | 10/2013 | Morse | .................... | A61K 36/87 |
| | | | | | 424/725 |
| 2016/0051611 | A1 * | 2/2016 | Banov | .................... | A61K 36/49 |
| | | | | | 424/769 |

FOREIGN PATENT DOCUMENTS

| | | | | |
|---|---|---|---|---|
| CN | 104586718 | A | * | 5/2015 |
| CN | 105012479 | A | * | 11/2015 |

(Continued)

OTHER PUBLICATIONS

"Press Release New Skinkicktm Skincare Line" by SkinKick, May 9, 2017 [Retrieved from the internet on Apr. 1, 2019] <URL: https://www.skinkick.com/press-release-new-skinkick-skincare-line/> (Year: 2017).*

(Continued)

*Primary Examiner* — Thomas J. Visone
(74) *Attorney, Agent, or Firm* — Edwin S. Flores; Daniel J. Chalker; Chalker Flores, LLP

(57) ABSTRACT

Disclosed are compositions and their use for the treatment of human skin, particularly facial skin, to alleviate the symptoms of cosmetic or dermatologic skin conditions. The compositions include black willow bark extract, cats claw extract, and dragon's blood extract. The compositions ameliorate skin conditions including acne, rosacea, blemish, dermatitis, eczema, or the like.

10 Claims, 6 Drawing Sheets

BEFORE

AFTER SKINKICK

(51) Int. Cl.

| | | |
|---|---|---|
| *A61K 36/47* | (2006.01) | |
| *A61K 36/48* | (2006.01) | |
| *A61K 36/58* | (2006.01) | |
| *A61K 36/61* | (2006.01) | |
| *A61K 36/74* | (2006.01) | |
| *A61K 36/889* | (2006.01) | |
| *A61P 17/10* | (2006.01) | |

(52) U.S. Cl.
CPC ............. *A61K 36/58* (2013.01); *A61K 36/61* (2013.01); *A61K 36/74* (2013.01); *A61K 36/889* (2013.01); *A61P 17/10* (2018.01)

(56) References Cited

FOREIGN PATENT DOCUMENTS

| CN | 106177100 | A | | 12/2016 |
|---|---|---|---|---|
| CN | 10651198 | A | * | 3/2017 |
| CN | 106491470 | A | * | 3/2017 |
| CN | 106491886 | A | | 3/2017 |
| CN | 106511198 | A | | 3/2017 |
| CN | 106963912 | A | * | 7/2017 |
| ES | 2525242 | B1 | * | 12/2014 |
| JP | 200327549 | A | * | 11/2000 |
| JP | 2000327549 | A | | 11/2000 |
| JP | 2007230977 | A | * | 9/2007 |
| WO | 2017206016 | A1 | | 12/2017 |
| WO | 2019136105 | A1 | | 7/2019 |

OTHER PUBLICATIONS

Della Valle V., "Uncaria tomentosa", Giornale Italiano Di Dermatologia E Venereologia, 2017, vol. 152, No. 6, pp. 651-657 (Year: 2017).*

Bennett, S. et al., "An extract of Salix nigra: an efficacious, safe remedy for problem skin", Active Ingredients, Conference Proceedings, Paris, Nov. 13-14, 1996, 161-170. (Year: 1996).*

Goncalves G.M.S et al., "Antioxidant and antimicrobial activities of propolis and agai (Euterpe oleracea Mart) extracts", Journal of Basic and Applied Pharmaceutical Sciences, 2011, vol. 32, No. 3, pp. 349-356 (Year: 2011).*

Amaral L. F. B. et al., I Cayyocar brasiliense supercritical C02 extract possesses antimicrobial and antioxidant properties useful for personal care products, BMC Complementary and Alternative Medicine, 2014, vol. 14, p. 73 [retrieved from internet on Mar. 21, 2019]<URL: (Year: 2014).*

Jones Kenneth, "Review of sangre de drago (Croton Lechleri)—a South American tree sap in the treatment of diarrhea, inflammation, insect bites, viral infections, and wounds: traditional uses to clinical research," Journal of Alternative and Complementary Medicine, vol. 9, No. 6, Dec. 1, 2003, pp. 877-896.

Amaral, et al., "Caryocar brasiliense supercritical CO2 extract possesses antimicrobial and antioxidant properties useful for personal care products," BMC Complementary & Alternative Medicine, vol. 14, No. 73, 2014, 7 pp.

Della, Valle V., "Uncaria tomentosa", Giornale Italiano Di Dermatologia E Venereologia, 2017, vol. 152, No. 6, pp. 651-657.

Goncalves, et al., "Antioxidant and antimicrobial activities of propolis and acai (Euterpe oleracea Mart) extracts," Journal of Basic and Applied Pharmaceutical Sciences, vol. 32(3), Oct. 2011, pp. 349-356.

International Search Report and Written Opinion for PCT/US19/012106 by Australian Patent Office dated Apr. 12, 2019, 17 pp.

Skinkick "Press Release—New Skinkicktm Skincare Line" by SkinKick, May 9, 2017 [Retrieved from the Internet on Apr. 1, 2019] <URL: https://www.skinkick.com/press-release-new-skinkick-skincare-line/>.

SkinKick Daily Archives: May 9, 2017, Press release-New Skinkick Skin Line, SkinKick, https://www.skinkick.com/press-release-new-skinkick-skincare-line/, pp. 1-7, May 9, 2017.

Decker, A., et al., "Over-the-counter Acne Treatments," The Journal of Clinical and Aesthetic Dermatology, vol. 5:5, May 2012, pp. 32-40.

Thiboutot, D., et al., "Acne Vulgaris and the Epidermal Barrier," The Journal of Clinical and Aesthetic Dermatology, vol. 6:1, Feb. 2013, pp. 18-24.

\* cited by examiner

BEFORE

AFTER SKINKICK

CLEAR SKIN

DAY 21

CALM SKIN

DAY 3

AGGRAVATED SKIN

BEFORE

TOPICAL SKIN CARE COMPOSITIONS

CROSS-REFERENCE TO RELATED APPLICATIONS

This application is the National Stage of International Application No. PCT/US2019/012106, filed on Jan. 2, 2019 claiming the priority to U.S. Provisional Application No. 62/612,940 filed on Jan. 2, 2018, the contents of each of which are incorporated by reference herein.

FIELD OF THE INVENTION

The present invention pertains to skin care compositions comprising one or more plant extracts. More specifically, the present invention pertains to skin care compositions comprising black willow bark extract, cat's claw extract, and dragon's blood extract, and their use for ameliorating certain skin conditions.

BACKGROUND OF THE INVENTION

Acne is a dermatological disorder prevalent in adolescence. It appears most commonly on the face and trunk of the patient. The basic lesion of acne is the comedo or "blackhead" of a pilosebaceous follicle. In its mildest form, only few comedones are present, but in its severe form, a multiplicity of severe, persistent comedones are present. Permanent scarring is frequently a consequence of the severe form of acne.

Acne is due essentially to the increased production, at puberty, of androgens such a testosterone, which stimulate the sebaceous glands in order to raise the production of sebum. Hyperkeratinization of the follicular duct is observed simultaneously, creating in the pilosebaceous follicle an environment which is rich in nutrients for the bacterial flora and which especially promotes the proliferation of diphtheroid anaerobic germs such as the Propionibacteria (e.g., acnes, granulosnm, avidum). As a result of bacterial growth in these horny impactions, the follicle ruptures, initiating the inflammatory phase of the disease which takes the form of pustules, papules, cysts, and nodules.

Acne treatments which are generally used are keratolytic agents such as salicylic acid or the derivatives thereof, to remove dead or hyperkeratinized skin, and antibacterial agents. A variety of methods have been used for the treatment of acne, including the use of peeling agents, hormone therapy for female patients, antibacterial therapy, and general surgical skin planing.

Although the systemic administration of hormones and antibacterials have been used with some success, until recently none of the topical treatments have been particularly effective. Therefore, there remains a need for alternative mild, "natural" topical skin care compositions that ameliorate skin conditions including acne, rosacea, blemish, dermatitis, eczema, or the like, while providing superior improvements to skin appearance and quality.

SUMMARY OF THE INVENTION

Various embodiments of a topical skin care composition are presented. In one embodiment, the present invention includes a topical skin care composition comprising black willow bark extract, cat's claw extract, and dragon's blood extract. In one aspect, the composition comprises from about 0.5 weight percent (wt %) to about 10 wt % of black willow bark extract. In another aspect, the composition comprises from about 0.2 wt % to about 7 wt % of cat's claw extract. In another aspect, the composition comprises from about 0.2 wt % to about 8 wt % of dragon's blood extract. In another aspect, the composition comprises from about 0.5 wt % to about 10 wt % of black willow bark extract and from about 0.2 wt % to about 7 wt % of cat's claw extract. In another aspect, the composition comprises from about 0.5 wt % to about 10 wt % of black willow bark extract and from about 0.2 wt % to about 8 wt % of dragon's blood extract. In another aspect, the composition comprises from about 0.2 wt % to about 7 wt % of cat's claw extract and from about 0.2 wt % to about 8 wt % of dragon's blood extract. In another aspect, the composition comprises from about 0.5 wt % to about 10 wt % of black willow bark extract, from about 0.2 wt % to about 7 wt % of cat's claw extract, and from about 0.2 wt % to about 8 wt % of dragon's blood extract. In another aspect, the composition is an emulsion, a gel, a cream, a lotion, a serum, or a solution. In another aspect, the composition further comprises at least one of: an emulsifier, a moisturizing agent, an essential oil, a sunscreen, a pharmaceutically active agent, a cosmetic ingredient, a triglyceride, a structuring agent, an antioxidant, a preservative, a gum, a polysaccharide, a polymer, a thickening agent, a gelling agent, or a vitamin. In another aspect, the emulsifier is cetearyl olivate or sorbitan olivate. In another aspect, the moisturizing agent is allantoin. In another aspect, the essential oil is *Copaifera officinalis* (balsam copaiba) resin. In another aspect, the composition comprises black willow bark extract, cat's claw extract, dragon's blood extract, cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incamata* (passionfruit) seed oil, *Caryocar brasiliense* fruit oil, tocopherol, phenoxyethanol, ethylhexylglycerin, and water. In another aspect, the composition comprises 0.5 wt % to about 10 wt % of black willow bark extract, from about 0.2 wt % to about 7 wt % of cat's claw extract, and from about 0.2 wt % to about 8 wt % of dragon's blood extract, from about 0.1 wt % to about 5 wt % cetearyl olivate, from about 0.1 wt % to about 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum* maritimum extract, from about 0.1 wt % to about 5 wt % hydrogenated vegetable oil, from about 0.1 wt % to about 5 wt % *Carapa guianensis* (andiroba)seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

In another embodiment, the present invention includes a method of treating a skin condition comprising topically applying a composition comprising black willow bark extract, cat's claw extract, and dragon's blood extract to skin in need thereof, wherein topical application of the composition to skin in need thereof ameliorates a skin condition. In one aspect, the skin condition is selected from the group consisting of dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions. In another aspect, the composition comprises from about 0.5 wt % to about 10 wt % of black willow bark extract. In another aspect, the composition comprises from about 0.2 wt % to about 7 wt % of cat's claw extract. In another aspect, the composition comprises from about 0.2 wt % to about 8 wt % of dragon's blood extract. In another aspect, the composition comprises from about 0.5 wt % to about 10 wt % of black willow bark extract and from about 0.2 wt % to about 7 wt % of cat's claw extract. In another aspect, the composition comprises from about 0.5 wt % to about 10 wt % of black willow bark extract and from about 0.2 wt % to about 8 wt % of dragon's blood extract. In another aspect, the composition comprises from about 0.2 wt % to about 7 wt % of cat's claw extract and from about 0.2 wt % to about 8 wt % of dragon's blood extract. In another aspect, the composition comprises from about 0.5 wt % to about 10 wt % of black willow bark extract, from about 0.2 wt % to about 7 wt % of cat's claw extract, and from about 0.2 wt % to about 8 wt % of dragon's blood extract. In another aspect, the composition is an emulsion, a gel, a cream, a lotion, a serum, or a solution. In another aspect, the method further comprising adding at least one of: an emulsifier, a moisturizing agent, an essential oil, a sunscreen, a pharmaceutically active agent, a cosmetic ingredient, a triglyceride, a structuring agent, an antioxidant, a preservative, a gum, a polysaccharide, a polymer, a thickening agent, a gelling agent, or a vitamin. In another aspect, the emulsifier is cetearyl olivate or sorbitan olivate. In another aspect, the moisturizing agent is allantoin. In another aspect, the essential oil is *Copaifera officinalis* (balsam copaiba) resin. In another aspect, the composition comprises black willow bark extract, cat's claw extract, dragon's blood extract, cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incamata* (passionfruit) seed oil, *Caryocar brasiliense* fruit oil, tocopherol, phenoxyethanol, ethylhexylglycerin, and water. In another aspect, the composition comprises 0.5 wt % to about 10 wt % of black willow bark extract, from about 0.2 wt % to about 7 wt % of cat's claw extract, and from about 0.2 wt % to about 8 wt % of dragon's blood extract, from about 0.1 wt % to about 5 wt % cetearyl olivate, from about 0.1 wt % to about 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum maritimum* extract, from about 0.1 wt % to about 5 wt % hydrogenated vegetable oil, from about 0.1 wt % to about 5 wt % *Carapa guianensis* (andiroba)seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

In another embodiment, the present invention includes a kit comprising a composition comprising black willow bark extract, cat's claw extract, and dragon's blood extract disposed within a container.

In another embodiment, the present invention includes a topical skin care composition comprising from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

In another embodiment, the present invention includes a maintenance therapy regime/regimen for inhibiting or treating moderate to severe acne vulgaris comprising: first topically administering to a subject in need of such treatment a therapeutically effective amount of a first topical skin care composition comprising black willow bark extract, cat's claw extract, and dragon's blood extract for a first predetermined period of time of 1 to 14 days; and subsequent to the first predetermined period of time of 1 to 14 days topically applying onto the affected skin area of the subject in need of such treatment, a therapeutically effective amount of a second topical skin care composition comprising balsam copaiba resin, Camu camu fruit extract, andiroba seed oil, acai fruit oil, pequi fruit oil for a second predetermined period of time up to 8 weeks. In one aspect, the topical skin care composition comprises from about 0.5 wt % to about 10 wt % of black willow bark extract, from about 0.2 wt % to about 7 wt % of cat's claw extract, and from about 0.2 wt % to about 8 wt % of dragon's blood extract formulated into an acceptable topical carrier. In another aspect, the fixed-dose combination is applied topically once a day. In another aspect, the acceptable topical carrier comprises an emulsion, a gel, an aqueous gel, a cream, a lotion, a serum, or a solution. In another aspect, the second topical skin care composition comprises from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

In another embodiment, the present invention includes a method of treating a skin condition selected from the group consisting of dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions with a composition comprising about 0.5 wt % to about 10 wt % of black willow bark extract, from about 0.2 wt % to about 7 wt % of cat's claw extract, and from about 0.2 wt % to about 8 wt % of dragon's blood extract formulated into an acceptable topical carrier.

In another embodiment, the present invention includes an anti-blemish and anti-aging composition comprising 0.5 wt % to about 10 wt % of black willow bark extract, from about 0.2 wt % to about 7 wt % of cat's claw extract, and from about 0.2 wt % to about 8 wt % of dragon's blood extract, 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

Also presented is a method of treating a skin condition by topically applying to skin in need thereof a composition according to the present invention, wherein topical application of the composition to skin in need thereof ameliorates a skin condition. The skin condition may be selected from dry skin, itchy skin, inflamed skin, erythema, sensitive skin, pruritus, blotches, fine lines or wrinkles, sun damaged skin, dermatitis, psoriasis, folliculitis, rosacea, acne, eczema, sunburns, burned skin, and skin-inflammatory skin conditions. In another embodiment, the dermatitis condition is selected from seborrheic dermatitis, nummular dermatitis, contact dermatitis, atopic dermatitis, exfoliative dermatitis, perioral dermatitis, and stasis dermatitis.

Also provided is a kit that includes the composition of the present invention disposed within a container.

BRIEF DESCRIPTION OF THE DRAWINGS

For a more complete understanding of the features and advantages of the present invention, reference is now made to the detailed description of the invention along with the accompanying figures and in which:

FIG. 4A is photograph that shows a subject before treatment with the present invention in which the subject had been using standard treatment commonly used in the industry, and FIG. 4B is a photograph that shows a subject after treatment with the present invention, and an inset with a close-up view of the resolution of the skin condition using the present invention.

FIG. 5A is photograph that shows a subject before treatment with the present invention in which the subject had been using standard treatment commonly used in the industry, and FIG. 5B is a photograph that shows a subject after treatment with the present invention, and an inset with a close-up view of the resolution of the skin condition using the present invention.

FIG. 6A is photograph that shows a subject before treatment with the present invention in which the subject had been using standard treatment commonly used in the industry for 15 years. By comparison, FIG. 6B is a photograph that shows a subject after treatment with the present invention, and an inset with a close-up view of the resolution of the skin condition using the present invention.

DETAILED DESCRIPTION OF THE INVENTION

Figure 1A:
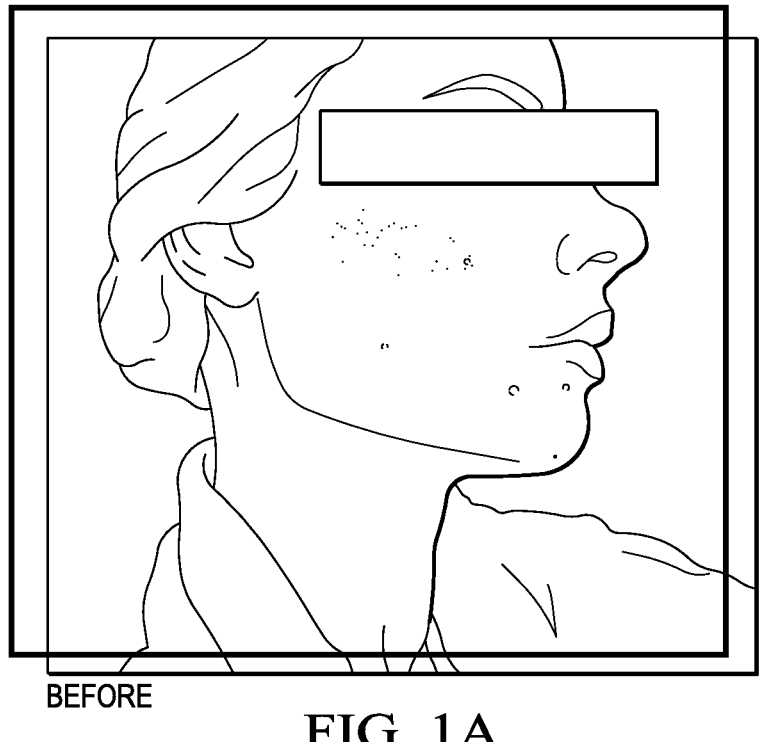
FIG. 1A is a photograph that shows a subject before treatment with the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "topical application" refers to a composition that is applied or spread onto the surface of the skin or other body surfaces. "Topical skin composition" includes compositions suitable for topical application on keratinous tissue. Such compositions are typically dermatologically-acceptable in that they do not have undue toxicity, incompatibility, instability, allergic response, and the like, when applied to the skin. Topical skin care compositions of the present invention can have a selected viscosity to avoid significant dripping or pooling after application to the skin.

As used herein, the term "keratinous tissue" includes keratin-containing layers disposed as the outermost protective covering of mammals and includes, but is not limited to, skin, hair, and nails.

As used herein, the term "non-volatile oil" refers to those substance that will not evaporate at ordinary or room temperature.

As used herein, the terms "mixture," "mix," and "mixing" or any variants of these terms, when used in the claims and/or the specification include: stirring, blending, dispersing, milling, homogenizing, and other similar methods of combining the ingredients of the present invention. The mixing of the components or ingredients of the disclosed compositions can form a solution. In other embodiments, the mixtures may not form a solution. The ingredients/components can also exist as undissolved colloidal suspensions.

As used herein, the terms "about" or "approximately" are defined as being close to as understood by one of ordinary skill in the art, and in one non-limiting embodiment the terms are defined to be within 10%, preferably within 5%, more preferably within 1%, and most preferably within 0.5%.

As used herein, the term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

As used herein, the terms "inhibiting" or "reducing" or any variation of these terms, when used in the claims and/or the specification includes any measurable decrease or complete inhibition to achieve a desired result.

As used herein, the term "effective amount" refers to that amount of the compositions and methods of the present invention effective to produce the intended effect of reducing, preventing and/or ameliorating dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and/or skin-inflammatory skin conditions. While not a limitation of the present invention, and solely for purposes of explanation, the dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions may be caused by bacteria, environmental conditions, hormonal changes, age, sun-exposure, exposure to humid or dry conditions, acute or chronic damage to the skin, diet, and combinations thereof.

As used herein, the terms "healthy skin" or "normal skin" refers to non-lesional skin, i.e., with no visually obvious erythema, edema, hyper-, hypo-, or uneven pigmentations, scale formation, xerosis, or blister formation. Histologically, healthy or normal skin refers to skin tissue with a morphological appearance comprising well-organized basal, spinous, and granular layers, and a coherent multi-layered stratum corneum. In addition, the normal or healthy epidermis comprises a terminally differentiated, stratified squamous epithelium with an undulating junction with the underlying dermal tissue. Normal or healthy skin typically includes no signs of fluid retention, cellular infiltration, hyper- or hypoproliferation of any cell types, mast cell degranulation, parakeratoses, etc., and implies normal dendritic processes for Langerhans cells and dermal dendrocytes. This appearance is documented in dermatological textbooks, for example, HISTOPATHOLOGY OF THE SKIN, Lever and Schaumburg-Lever (eds.), J.B. Lippincott Company (1991) and TEXTBOOK OF DERMATOLOGY, Champion et al. (eds.), 5th Ed. Blackwell Scientific Publications (1992), especially Chapter 3 "Anatomy and Organization of Human Skin"; PHYSIOLOGY, BIOCHEMISTRY AND MOLECULAR BIOLOGY OF THE SKIN, VOLS. I AND II, Goldsmith (ed.), Oxford Press (1991), relevant portions incorporated herein by reference.

In one embodiment, compositions of the present invention can be pharmaceutically or cosmetically elegant. As used herein, the terms "pharmaceutically elegant" and/or "cosmetically elegant" describes a composition that has particular tactile properties that feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or the moisture retaining properties of the composition.

The composition of the present invention is typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the composition may be formulated to provide, e.g., maximum and/or consistent dosing for topical administration. While the composition may be administered alone, it will generally be provided in a stable salt form mixed with a pharmaceutically acceptable carrier. The carrier may be solid or liquid, depending on the type and/or location of administration selected.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); Remington: The Science and Practice of Pharmacy, Pharmaceutical Press; 22nd Edition (2012); all of which are incorporated by reference, and the like, relevant portions incorporated herein by reference.

The composition may be administered in the form of a topical delivery system, which may include those pharmaceutical salts, buffers, diluents, extenders, excipients and/or carriers (collectively referred to herein as a pharmaceutically acceptable carrier or carrier materials, commonly used for topical administration. One such non-limiting example is a liposomal delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like. The topical composition may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the composition may be coupled one or more biodegradable polymers to achieve controlled release of the composition, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

In certain embodiments, the present invention overcomes known problems with the prior art, in particular the need to avoid harsh chemical treatments and/or peels that include benzoyl peroxide, salicylic acid, adapalene, and/or retinol. Thus, in certain embodiments, the composition of the present invention is free or substantially free of benzoyl peroxide, salicylic acid, adapalene, and/or retinol. Benzoyl peroxide, salicylic acid, adapalene, and/or retinol are known to have significant side-effects, including severe irritation of the skin, allergic reactions, and even throat tightness, breathing problems, or swelling of the eyes, face, lips or tongue associated with such allergic reactions.

The present invention is an effective alternative to the use of compositions and ingredients currently used to treat acne, rosacea, blemish, dermatitis, eczema, and other skin conditions.

The following examples of specific embodiments of the invention are for purposes of illustrating the invention and are not intended to limit the scope of the invention.

In one aspect, the topical skin care composition includes black willow bark extract, cat's claw extract, and dragon's blood extract. In one embodiment, the composition includes from about 0.5 weight percent of the total weight (wt %) to about 10 wt % of black willow bark extract. In one embodiment, the composition includes from about 0.2 wt % to about 7 wt % of cat's claw extract. In one embodiment, the composition includes from about 0.2 wt % to about 8 wt % of dragon's blood extract. As used herein, the terms "weight percent" or "wt %" refers to the weight percent of the component relative to the total weight of the composition.

In one embodiment, the composition includes from about 0.5 wt % to about 10 wt % of black willow bark extract and from about 0.2 wt % to about 7 wt % of cat's claw extract. In one embodiment, the composition includes from about 0.5 wt % to about 10 wt % of black willow bark extract and from about 0.2 wt % to about 8 wt % of dragon's blood extract. In one embodiment, the composition includes from about 0.2 wt % to about 7 wt % of cat's claw extract and from about 0.2 wt % to about 8 wt % of dragon's blood extract.

In one embodiment, the composition includes from about 0.5 wt % to about 10 wt % of black willow bark extract, from about 0.2 wt % to about 7 wt % of cat's claw extract, and from about 0.2 wt % to about 8 wt % of dragon's blood extract.

In one embodiment, the composition may include from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

In one embodiment, the composition includes black willow bark extract, cat's claw extract, dragon's blood extract, cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incarnata* (passionfruit) seed oil, *Caryocar brasiliense* fruit oil, tocopherol, phenoxyethanol, ethylhexylglycerin, and water.

The composition may include 0.5 wt % to about 10 wt % of black willow bark extract, from about 0.2 wt % to about 7 wt % of cat's claw extract, and from about 0.2 wt % to about 8 wt % of dragon's blood extract, from about 0.1 wt % to about 5 wt % cetearyl olivate, from about 0.1 wt % to about 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum maritimum* extract, from about 0.1 wt % to about 5 wt % hydrogenated vegetable oil, from about 0.1 wt % to about 5 wt % *Carapa guianensis* (andiroba)seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

Black willow bark extract comes from the bark of black willow tree (*Salix nigra*). The extract contains natural beta hydroxyl acids (BHA) and is reported to have natural anti-inflammatory and antiseptic properties. One of these BHA's is a natural form of salicylic acid that is a natural exfoliant and is used in many acne treatments because of its ability to help skin shed dead cells and clear pores; it can also stimulate new cell formation. Willow bark extract also contains phenolic acids, such as salicin, salicortin, fragilin, populin, triandrin, and vimalin, as well as flavonoids, tannins (gallotannins and catechin-type tannins), and minerals, which all allow it to aid in skin rejuvenation.

Cat's claw extract is derived from Uncaria tomentosa, a woody vine native to the tropical jungles of South and Central America. The name, cat's claw, comes from the thorns on the plant's leaves that have a hook-like shape and look like the claws of a cat. Cat's claw is found to have powerful anti-inflammatory and antioxidant effects. Cat's claw is used traditionally in Peruvian medicine for the treatment of a wide range of health problems, particularly digestive complaints and arthritis and to treat wounds, stomach problems, and cancer. The oxindole alkaloids, found in the bark and roots of cat's claw, have been documented to stimulate the immune system and have a variety of different medicinal and healing properties. The most immunologically active alkaloid is believed to be isopteropodin (Isomer A), which increases the immune response in the body and act as antioxidants to rid the body of free radicals. Compounds found in cat's claw may also work to kill viruses, bacteria, and other microorganisms that cause disease.

Dragon's blood extract is a bright red resin that is obtained from different species of a number of distinct plant genera: *Croton, Dracaena, Daemonorops, Calamus rotang,* and *Pterocarpus.* In one embodiment, dragon's blood extract is obtained from *Dracaena cambodiana* trees. In another embodiment, dragon's blood extract is obtained from *Croton uechleri* trees. The indigenous local Amazonians call this botanical "dragon's blood" because the red sap that oozes from the tree when it is cut has the appearance of blood. Both *Dracaena* and *Daemonorops* resins are still often marketed today as dragon's blood, with little or no distinction being made between the plant sources; however, the resin obtained from *Daemonorops* has become the most commonly sold type in modern times, often in the form of large balls of resin. The red resin has been in continuous use since ancient times as varnish, medicine, incense, and dye. Over 50 clinical studies have been reported and claim that dragon's blood has the potential to promote skin repair and act as antiseptic because it is antibacterial, anti-inflammatory and anti-microbial properties. The red sap dries on the skin and forms a so-called "second skin" which is a protective shield to keep the environment at bay and to accelerate regeneration at the same time. It also helps to reduce the appearance of redness and improve the beauty of the skin.

Balsam copaiba, an oily oleo-resin obtained from the trunk of the tree, has a very long history of use medicinally. It was widely used by the native peoples prior to the Europeans reaching South America, and these uses were soon taken up by the Europeans. The resin is especially valued for its ability to counter mucous in the chest and genitourinary system. Both the resin and the bark are anodyne, antacid, antibacterial, antifungal, anti-inflammatory, antimicrobial, astringent, cytostatic, demulcent, digestive, disinfectant, diuretic, expectorant, mildly laxative, vermifuge and vulnerary. The resin obtained from the trunk contains a number of medically active constituents including 30-90% essential oils and unusual condensed tannins. The essential oil contains alpha- and beta-caryophyllene, sesquiterpenes, resins and terpenic acids. It improves the digestion, has diuretic and expectorant effects, and controls bacterial infections. Much of the clinical research performed to date has verified the traditional uses of copaiba. It has, for instance, been shown to be highly effective as a topical wound healer and anti-inflammatory agent. The anti-inflammatory effect is mainly due to the sesquiterpenes, particularly caryophyllene which has also demonstrated effective pain-relieving properties, antifungal properties against nail fungus and gastroprotective properties. The resin as a whole (and, particularly, two of its diterpenes—copalic acid and kaurenic acid) has demonstrated significant antimicrobial activity against gram-positive bacteria. Externally, the resin is used in the treatment of a range of skin problems including insect bites, eczema, chilblains, sores, and psoriasis.

*Tamarindus indica* (Tamarind) seed polysaccharide (TSP) is a natural polysaccharide polymer obtained from the seeds of *Tamarindus indica*, an evergreen plant which is very common in India, Africa, and throughout the Far East, where it is mainly grown as food. The fruit contains large seeds with a high percentage of polysaccharides, which have the function of accumulating and preserving vital energy-giving substances. It is used traditionally in abdominal pain, diarrhea and dysentery, helminthes infections, wound healing, malaria and fever, constipation, inflammation, cell cytotoxicity, gonorrhea, and eye diseases. It has numerous chemical values and is rich in phytochemicals, and hence the plant is reported to possess antidiabetic activity, antimicrobial activity, antivenomic activity, antioxidant activity, antimalarial activity, hepatoprotective activity, antiasthmatic activity, laxative activity, and anti-hyperlipidemic activity.

*Myrciaria dubia* commonly known as camu camu, Camu-Camu, cacari, or camo camo, is a small bushy riverside tree from the Amazon rainforest in Peru and Brazil, which bears a red/purple cherry-like fruit. The high vitamin C content, on the order of 2-3% of fresh weight, is the most important property of the fruit.

*Crithmum maritimum* is also known as samphire, rock samphire, or sea fennel. *Crithmum maritimum* is an edible wild plant. It is found on southern and western coasts of Britain and Ireland, on Mediterranean and western coasts of Europe including the Canary Islands, North Africa, and the Black Sea. The plant contains vitamin C (ascorbic acid and dehydroascorbic acid), polyacetylenes (including falcarinol and falcarindiol), flavonoids (diosmin), furanocoumarins, pectin and the minerals zinc, iron, magnesium, iodine, and sulfates. In addition, the essential oil extracted from *Crithmum maritimum* contains the substances geranyl acetate, dillapiole, sabin, limonene, thymol methyl ether and gamma terpinene.

*Carapa guianensis*, also known as andiroba, is used in popular medicine in Brazil and other countries are encompassing the Amazon rainforest. Virtually all parts of the andiroba tree are utilized, including the seed's oil, which is employed to treat inflammation and infections. The medicinal properties of *C. guianensis* have been attributed to the presence of limonoids, which are tetranortriterpenoids. The oil obtained from *C. guianensis* seeds contains different tetranortriterpenoids, including 6α-acetoxygedunin, 7-deacetoxy-7-oxogedunin, and robin, gedunin, and methyl-angolensate. The seeds oil and this fraction of tetranortriterpenoids present marked anti-inflammatory and anti-allergic properties.

*Euterpe oleracea* (açai) has been acclaimed to have a wide range of health-promoting and therapeutic benefits due to its reportedly high levels of antioxidants. *Euterpe oleracea* has a history of use as a medicinal plant and as a staple food in many parts of Brazil. Traditionally, it has been used to treat fevers, skin complications, digestive disorders and parasitic infections. *Euterpe oleracea* has also been of great economic importance in Brazil. This is based on a relatively high content of polyphenols, which in turn has been linked to a range of antioxidant, anti-inflammatory, antiproliferative, and cardioprotective properties.

*Melaleuca alternifolia* leaf oil, also known as Tea Tree oil or *Melaleuca* oil, is one of the most widely used and extensively researched essential oils. Of all of the properties claimed for *Melaleuca* oil, its antimicrobial activity has received the most attention. The earliest reported use of the *M. alternifolia* plant that presumably exploited this property was the traditional use by the Bundjalung Aborigines of northern New South Wales. Crushed leaves of "tea trees" were inhaled to treat coughs and colds or were sprinkled on wounds, after which a poultice was applied. In addition, tea tree leaves were soaked to make an infusion to treat sore throats or skin ailments. Contemporary data show that the broad-spectrum activity of *Melaleuca* oil includes antibacterial, antifungal, antiviral, and antiprotozoal activities.

*Caryocar brasiliense*, known as pequi, is an edible fruit popular in some areas of Brazil, especially in Brazil's central-west region. Pequi essential oil can be extracted from the nuts/seeds inside the mesocarp of the pequi fruit. This essential oil is often included in traditional shampoos and moisturizers in Brazil, but it is starting to gain ground on the international market as well. Furthermore, the high content of tocopherol and vitamin A in pequi means that the skin and hair are protected due to the antioxidant properties of these compounds. Consuming pequi can keep skin from showing blemishes, improve scar healing, add a rich glow to the skin, and prevent signs of premature aging. It has also traditionally been used for treating eczema and skin lesions.

A person of ordinary skill in the art would be able to isolate any one of the extracts identified above from parts of the corresponding plant by using any suitable method known in the art. In one non-limiting example, the plant (or any part of the plant such as the leaves, stems, bark, roots, fruit, flowers or flower buds, seeds, seed pods, sap, whole plant, etc.) can be disrupted by mechanical means which results in a puree. The puree is then processed to be substantially free of impurities or undesired solids. The puree can then be poured into a shallow vessel and quickly exposed to low temperature, i.e., flash frozen, for example at −20° C. or lower, preferably under a vacuum for removal of water content (lyophilization). The resultant extract can then be used in the compositions of the present invention.

In other aspects, aqueous, alcoholic, or oil based extraction techniques, or combinations thereof, can be used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then subjected to a desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-fluoro-carbon solvents).

In some embodiments, the composition is formulated as topical skin composition. The composition can be a lotion, a cream, a gel, a emulsion (e.g., oil-in-water, water-in-oil, silicone-in water, water-in-silicone, water-in-oil-in-water, oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, etc. The composition can be in the powdered form (e.g., dried, lyophilized, particulate, etc.). The composition can have a dermatologically acceptable vehicle or carrier for the plant, plant part, or extract thereof. The composition can further include a moisturizing agent, an antioxidant, a structuring or thickening agent, and/or an emulsifier (examples of each of these ingredients is provided below). The composition can further include a silicone containing compound and/or a sunscreen agent. The compositions of the present invention can also include any one of, any combination of, or all of the following additional ingredients: water, a preservative, a silicone containing compound, an essential oil, a structuring agent, a vitamin, a pharmaceutical ingredient, or an antioxidant, or any combination of such ingredients or mixtures of such ingredients. In certain aspects, the composition can include at least two, three, four, five, six, seven, eight, nine, ten, or all of these additional ingredients identified in the previous sentences. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

In some embodiments, the composition may further include one or more emulsifiers. Emulsifiers can reduce the interfacial tension between phases and improve the formulation and stability of an emulsion. The emulsifier may include a non-ionic emulsifier, an anionic emulsifier, a cationic emulsifier, a Zwitterionic emulsifier or a combination thereof. Non-limiting examples of emulsifiers include esters of glycerin, esters of propylene glycol, fatty acid esters of polyeth ylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethyl ene glycol 5 soya sterol, Steareth-2, Steareth-20, Steareth-21, ceteareth-20. PPG-2 methylglucose ether distearate, ceteth 10, polysorbate 80, cetyl phosphate, potassium cetyl phosphate, diethanolamine cetyl phosphate, polysorbate 60, glyceryl Stearate, PEG-100 stearate, and mixtures thereof. In one embodiment, the non-ionic emulsifier is cetearyl olivate or sorbitan olivate. In another embodiment, the emulsifier is present in an amount of from about 0.1 wt % to about 4.0 wt %.

In one embodiment, the composition further includes a moisturizing agent. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol. In one embodiment, the moisturizing agent is glycerin. In another embodiment, the moisturizing agent is present in an amount of from about 0.5 wt % to about 6.0 wt %.

Other examples include acetylated lanolin, acetylated lanolin alcohol, alanine, algae extract, aloe barbadensis, aloe-barbadensis extract, aloe barbadensis gel, althea officinalis extract, apricot (*Prunus armeniaca*) kernel oil, arginine, arginine aspartate, arnica montana extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (*Oenothera biennis*) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil.

Additional non-limiting examples of moisturizing agents may include PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Trificum vulgare*) germ oil, and ylang ylang (*Cananga odorata*) oil. In one embodiment, the moisturizing agent may be allantoin. In another embodiment, the moisturizing agent is present in the composition in an amount of from about 0.5 wt % to about 6.0 wt %.

In some embodiments, the composition may further include a thickening agent. Thickening agents, including thickener or gelling agents, include substances which that can increase the viscosity of a composition. Thickening agents include those that can increase the viscosity of a composition without substantially modifying the efficacy of the active ingredient within the composition. Thickening agents can also increase the stability of the compositions of the present invention. In certain aspects of the present invention, thickening agents include hydrogenated polyisobutene or trihydroxy stearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see CTFA International Cosmetic Ingredient Dictionary, Fourth Edition, 1991, pp. 12 and 80). Examples of commercially available carboxylic acid polymers include carbomers, which are homopolymers of acrylic acid crosslinked with allyl ethers of sucrose or pentaerythritol (e.g., Carbopol™ 900 series from B. F. Goodrich). Non-limiting examples of crosslinked polyacrylate polymers include cationic and nonionic polymers.

Non-limiting examples of polyacrylamide polymers (including nonionic polyacrylamide polymers including substituted branched or unbranched polymers) include polyacrylamide, isoparaffin and Laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxy late, hydroxyethylcellulose, hydroxyethyl ethylcellulose, hydroxypropyl cellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer are hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present compositions include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof. In one embodiment, the thickening agent is *Chondrus crispus* (carrageenan) extract. In another embodiment, the thickening agent is present in the composition in an amount of from about 0.1 wt % to about 4.5 wt %.

In some embodiments, the composition further includes an essential oil. Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age, they can oxidize and become darker. Essential oils are insoluble in water and are soluble in alcohol, ether, fixed oils (vegetal), and other organic solvents. Typical physical characteristics found in essential oils include boiling points that vary from about 160° C. to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention. In one embodiment, the essential oil may be *Copaifera officinalis* (balsam copaiba) resin. In another embodiment, the essential oil component is present in an amount of from about 0.1 wt % to about 2.5 wt %.

In some embodiments, the composition may further include a preservative. Non-limiting examples of preservatives may include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, ethylhexylglycerinbenzyl alcohol, chlorobutanol, phenol, sorbic acid, thimerosal or combinations thereof. In some embodiments, the preservative in the compositions is phenoxyethanol. In some embodiments, the preservative in the compositions is ethylhexylglycerin. In another embodiment, the preservative component is present in an amount of from about 0.1 wt % to about 1.0 wt %.

In some embodiments, the composition may also include an antioxidant. Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamyihydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical antioxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite. In one embodiment, the antioxidant is tocopherol. In another embodiment, the antioxidant component is present in an amount of from about 0.1 wt % to about 10 wt %.

In some embodiments, the composition may also include a structuring agent. Structuring agent, in certain aspects, assists in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

In some embodiments, the compositions may additionally include a triglyceride. Non-limiting examples include small, medium, and large chain triglycerides. In certain aspects, the triglyceride is a medium chain triglyceride (e.g., caprylic/capric triglyceride).

In some embodiments, the compositions may also include a UV absorption agent. UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octyl-methoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethyl-amino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include kaolin, talc, petrolatum and metal oxides (e.g., titanium dioxide and zinc oxide).

In some embodiments, the composition may also include a cosmetic ingredient. A wide variety of non-limiting cosmetic ingredients described in the CTFA International Cosmetic Ingredient Dictionary and Handbook (2004 and 2008) can be used. Non-limiting examples of cosmetic ingredients include fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g., A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *Ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylpara-ben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethi-cone, hyaluronic acid, and dipotassium glycyrrhizate).

In some embodiments, the compositions may further include a pharmaceutical active agent. Non-limiting examples of pharmaceutical active agents include anti-acne agents, agents used to treat rosacea, analgesics, anesthetics, anorectals, antihistamines, anti-inflammatory agents includ-ing non-steroidal anti-inflammatory drugs, antibiotics, anti-fungals, antivirals, antimicrobials, anti-cancer actives, scabi-cides, pediculicides, antineoplastics, antiperspirants, antipruritics, antpsoriatic agents, antiseborrheic agents, bio-logically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

Also presented herein are methods of treating a skin condition by topically applying to skin in need thereof a composition of the present invention, wherein topical appli-cation of the composition to skin in need thereof treats or ameliorates the skin condition. The composition can be applied to a fine line or wrinkle, dry, flaky, or itchy skin, inflamed skin, and other skin-associated disorders disclosed throughout this application. Non-limiting examples of skin conditions include dry skin, itchy skin, inflamed skin, ery-thema, sensitive skin, pruritus, blotches, fine lines or wrinkles, sun damaged skin, dermatitis (including, but not limited to seborrheic dermatitis, nummular dermatitis, con-tact dermatitis, atopic dermatitis, exfoliative dermatitis, perioral dermatitis, and stasis dermatitis), psoriasis, follicu-litis, rosacea, acne, eczema, sunburns, burned skin, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identify-ing a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

Example 1

Figure 1B:
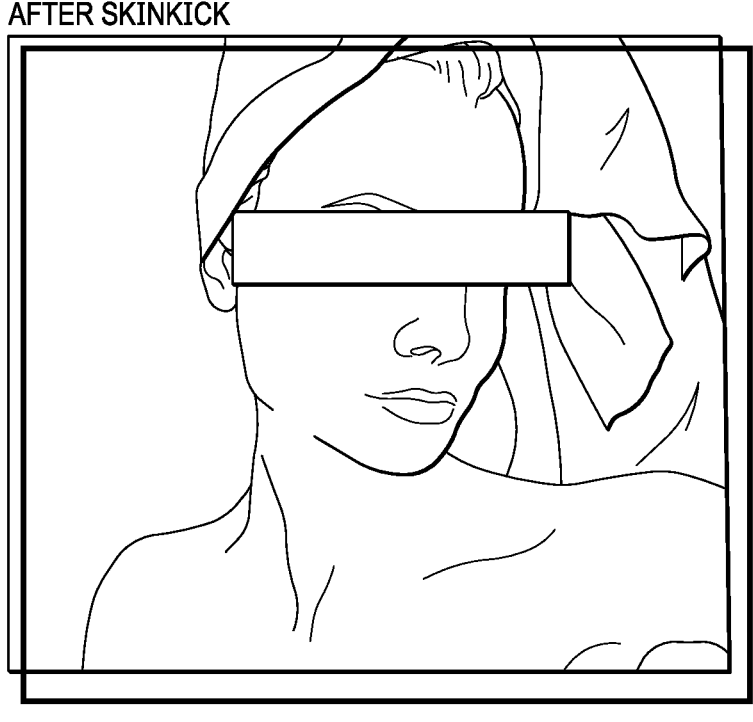
FIG. 1B is a photograph that shows a subject after treatment with the present invention.

A 23 year old female, with a history of acne and skin blemishes, was treated with the composition of the present invention. In this example the composition included 0.5 wt % to about 10 wt % of black willow bark extract, from about 0.2 wt % to about 7 wt % of cat's claw extract, and from about 0.2 wt % to about 8 wt % of dragon's blood extract. FIG. 1A is a before, and FIG. 1B and after treatment following treatment for at least 14 days using the present invention. FIG. 1A clearly shows widespread acne and other blemishes across the cheek area. FIG. 1B shows the com-plete resolution of the acne and other blemishes across the same cheek area shown in FIG. 1A.

Example 2

Figure 2C:
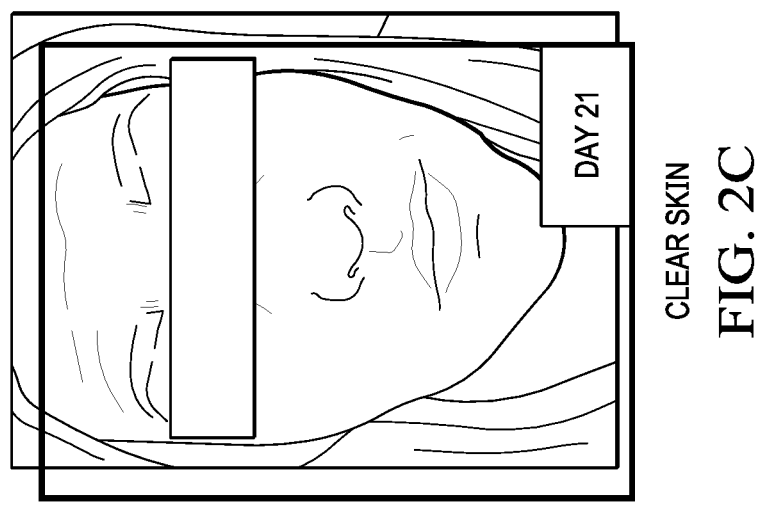
FIG. 2C shows the subject after 21 days of treatment showing complete resolution.
Figure 2B:
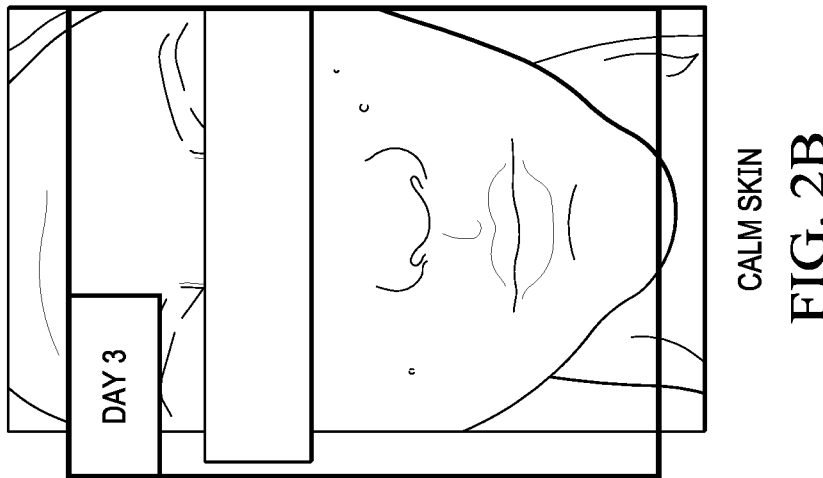
FIG. 2B is a photograph that shows a subject after initial treatment with the present invention.
Figure 2A:
FIG. 2A is a photograph that shows a subject before treatment with the present invention.

A 29 year old female, with a history of acne and skin blemishes, was treated with the composition of the present invention. In this example, the subject used the two-step method of the present invention, in which a first composition included 0.5 wt % to about 10 wt % of black willow bark extract, from about 0.2 wt % to about 7 wt % of cat's claw extract, and from about 0.2 wt % to about 8 wt % of dragon's blood extract. The second composition included 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil. The compositions are also referred to herein as SkinKick. FIG. 2A is a before photograph, FIG. 2B shows that the skin after 3 days treatment in which the skin is no longer widely red and aggravated (as seen in FIG. 21), and FIG. 2C shows the skin after treatment following treatment for 21 days using the present invention. FIG. 2A clearly shows widespread acne and other blemishes across the facial area and further includes significant seborrheic dermatitis. FIG. 2B shows the face 3 days after the start of treatment with the present invention in which the seborrheic dermatitis has been reduced or eliminated. After 21 days, FIG. 2C shops the complete resolution of the acne and other blem-ishes across the same area shown in FIGS. 2A and 2C. The subject described the composition as "self-esteem in a bottle". The subject had been dealing with aggravated skin and blemishes when she decided to the two-step method of the present invention. The subject noticed that after only 3 days, her skin had calmed down significantly and her blemishes were clearing. By day 21, the subject's skin was clear, refreshed, and glowing. The subject felt that she "feels empowered and stands tall". As regards her condition, the subject further stated, "within 2 days, my redness went down. SkinKick totally changed my skin. It's really a game-changer!".

Comparative Example 3

Figure 3A:
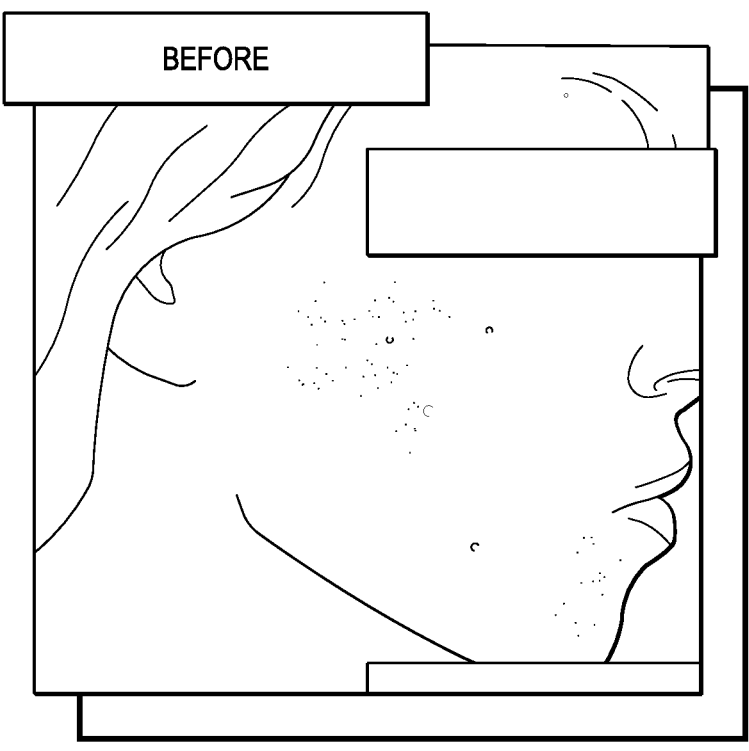
FIG. 3A is a photograph that shows a subject before treatment with the present invention.
Figure 3B:
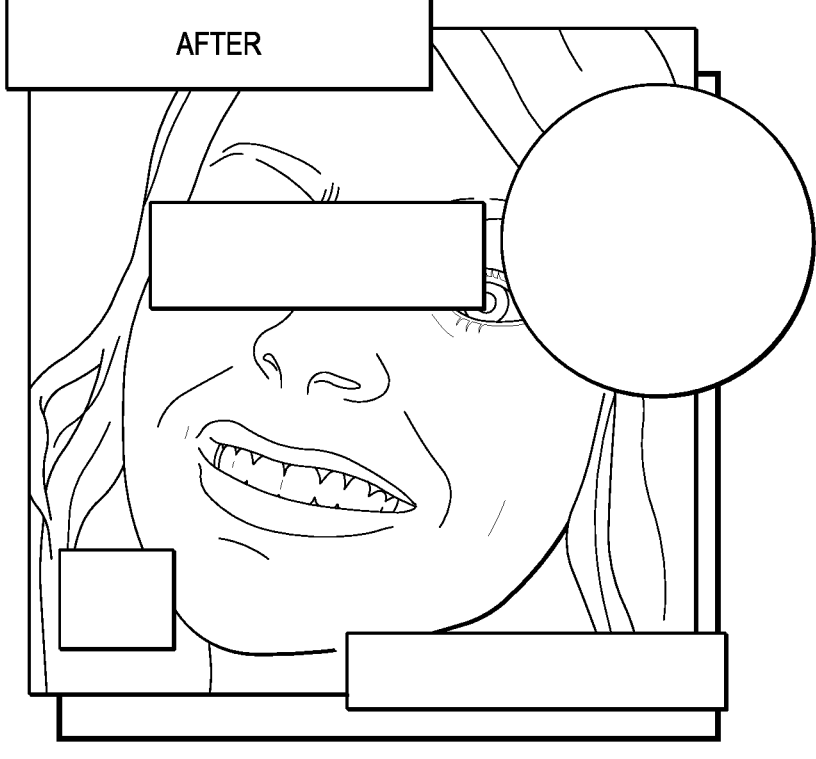
FIG. 3B is a photograph that shows a subject after treatment with the present invention.

A 39 year old female, with a history of acne and skin blemishes, with small areas of seborrheic dermatitis and/or allergic reactions, was treated with the composition of the present invention. Previously, the subject had been using, for a 3 year period, a composition that included benzoyl per-oxide and salicylic acid, widely used in the industry. The comparative composition includes a three-step anti-acne kit that includes a cleanser, a toner and a lotion. Each of the composition previously used by the subject included active agents such as benzoyl peroxide and salicylic acid. In this example the composition used by the subject included 0.5 wt % to about 10 wt % of black willow bark extract, from about 0.2 wt % to about 7 wt % of cat's claw extract, and from about 0.2 wt % to about 8 wt % of dragon's blood extract. FIG. 3A is a before photograph following 3 years of treatment with the prior art three-step anti-acne kit consisting of a cleanser, toner and lotion (benzoyl peroxide and salicylic acid). By comparison, FIG. 3B is a photograph and after treatment with the present invention. FIG. 3A clearly shows widespread acne and other blemishes across the cheek area. FIG. 3B shows the complete resolution of the acne and other blemishes across the entire facila area shown in FIG. 3A. FIG. 3B further includes an inset that shows a close-up view that clearly shows the complete resolution of the acne and other blemishes.

Comparative Example 1

Figure 4A:
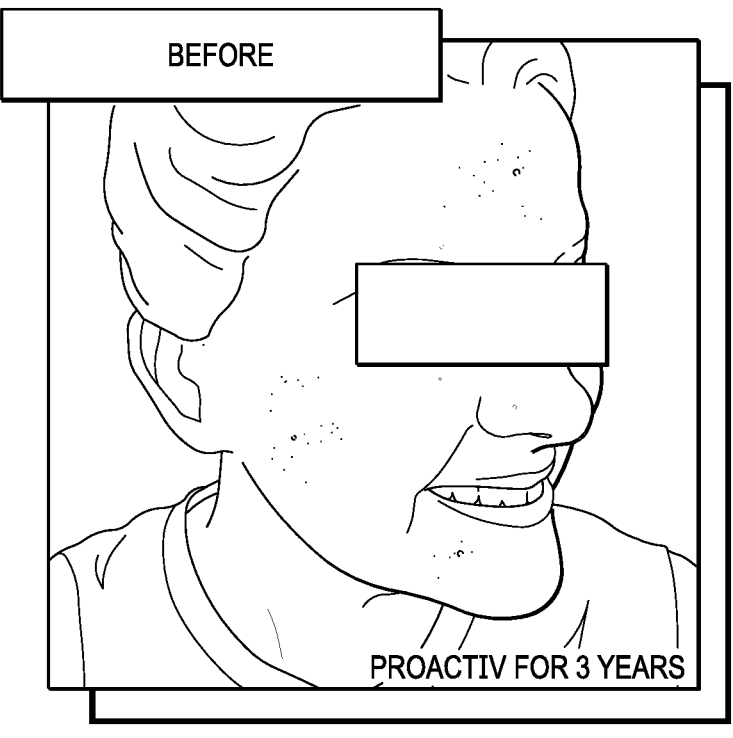
FIGS. 4A and 4B show a comparative example of the present invention versus existing industry standard treatment.
Figure 4B:
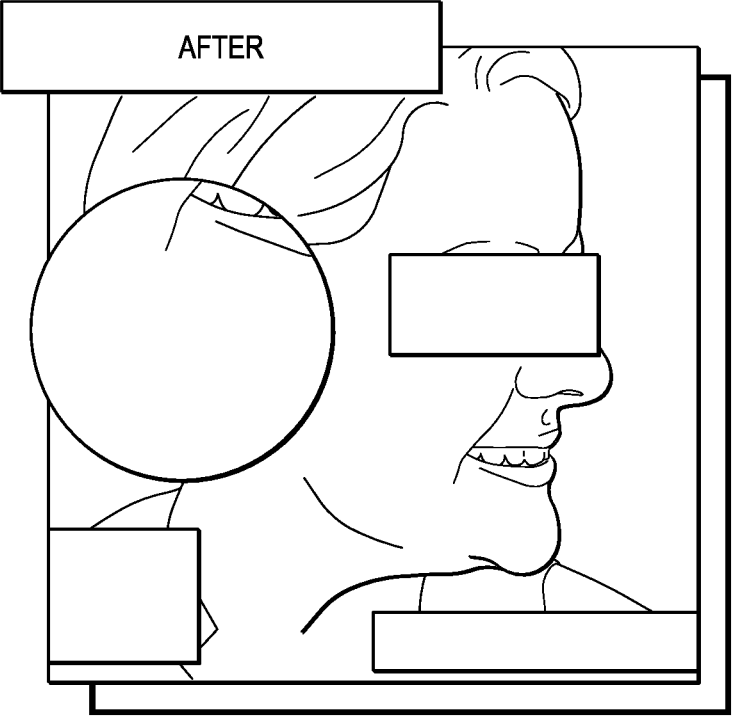

A 19 year old female, with a history of acne and skin blemishes, with small areas of seborrheic dermatitis and/or allergic reactions, was treated with the composition of the present invention. Previously, the subject had been using, for at least 3 years, a composition that included benzoyl peroxide and salicylic acid, widely used in the industry. The comparative composition includes a three-step anti-acne kit that includes a cleanser, a toner and a lotion. Each of the composition previously used by the subject included active agents such as benzoyl peroxide and salicylic acid. In this example the composition used by the subject included 0.5 wt % to about 10 wt % of black willow bark extract, from about 0.2 wt % to about 7 wt % of cat's claw extract, and from about 0.2 wt % to about 8 wt % of dragon's blood extract. FIG. 4A is a before photograph following 3 years of treatment with the prior art three-step anti-acne kit consisting of a cleanser, toner and lotion (benzoyl peroxide and salicylic acid). By comparison, FIG. 4B is a photograph and after treatment with the present invention. FIG. 4A clearly shows widespread acne and other blemishes across the cheek area. FIG. 4B shows the complete resolution of the acne and other blemishes across the entire facila area shown in FIG. 4A. FIG. 4B further includes an inset that shows a close-up view that clearly shows the complete resolution of the acne and other blemishes. The subject stated, "To anyone looking to change your skin for the better: keep reading . . . I discovered this new skincare, and it has completely changed my face for the good! It has cleared it up, made it so soft, and has brightened my skin, and I saw results in the first day! Finally a skincare I believe in! I think EVERYONE needs to get this in their hands asap. Seriously could not be more in love with this product!"

Comparative Example 2

Figure 5A:
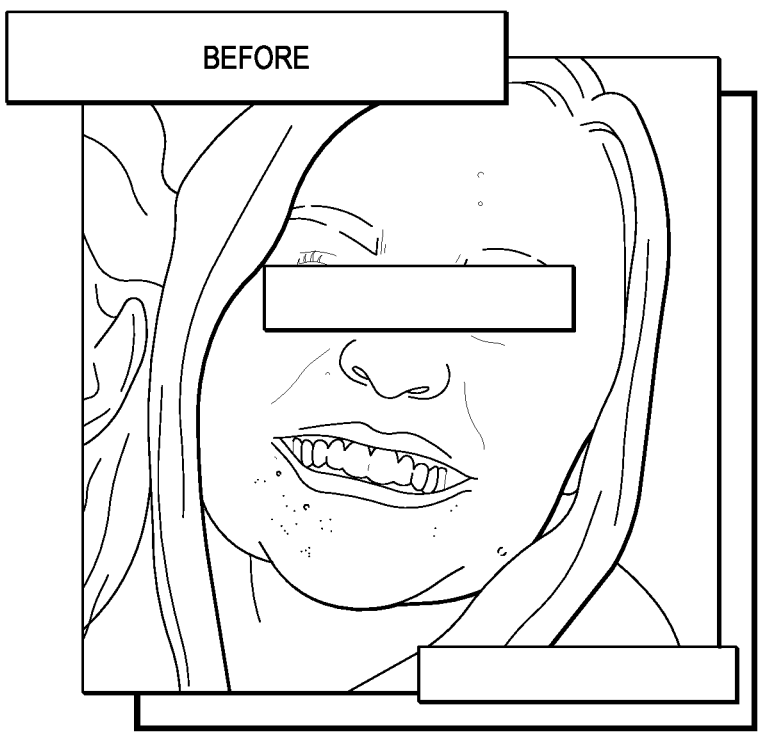
FIGS. 5A and 5B show a comparative example of the present invention versus existing industry standard treatment.
Figure 5B:
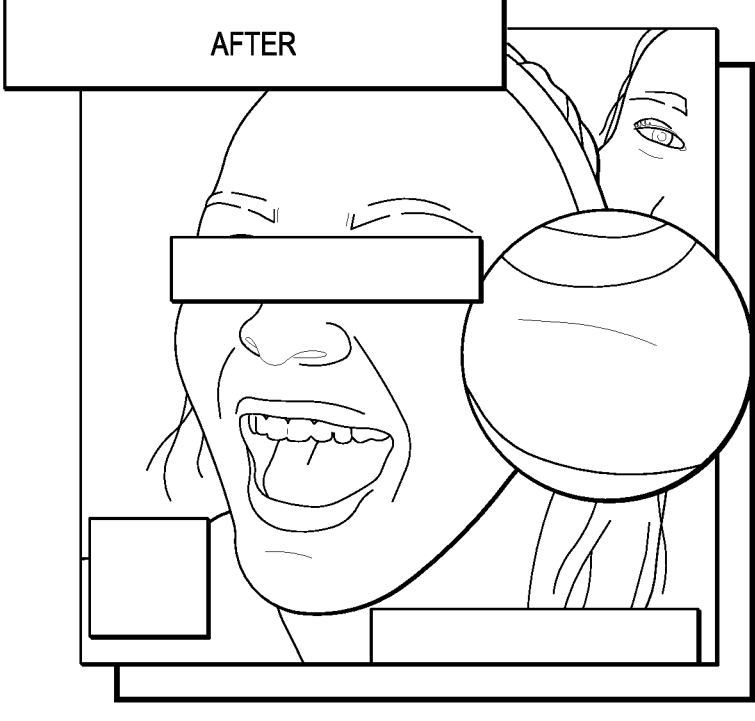

A 15 year old female, with a history of acne and skin blemishes, with small areas of seborrheic dermatitis and/or allergic reactions, was treated with the composition of the present invention. Previously, the subject had been using, for at least 3 years, a composition that included benzoyl peroxide and salicylic acid, widely used in the industry. The comparative composition includes a three-step anti-acne kit that includes a cleanser, a toner and a lotion. Each of the composition previously used by the subject included active agents such as benzoyl peroxide and salicylic acid. In this example the composition used by the subject included 0.5 wt % to about 10 wt % of black willow bark extract, from about 0.2 wt % to about 7 wt % of cat's claw extract, and from about 0.2 wt % to about 8 wt % of dragon's blood extract. FIG. 5A is a before photograph following 3 years of treatment with the prior art three-step anti-acne kit consisting of a cleanser, toner and lotion (benzoyl peroxide and salicylic acid). By comparison, FIG. 5B is a photograph and after just 3 days of treatment with the present invention. FIG. 5A clearly shows widespread acne and other blemishes across the cheek area. FIG. 5B shows the complete resolution of the acne and other blemishes across the entire facila area shown in FIG. 5A. FIG. 5B further includes an inset that shows a close-up view that clearly shows the almost complete resolution of the acne and other blemishes in just 3 days. The subject's parent stated, "We love this product! I started my daughter on this product after we had tried EVERYTHING else and were headed down the dangerous path of doing accutane. I just couldn't put her through it without at least giving SkinKick a try first. We are so glad we did! Unlike some others, it didn't happen overnight, but it DID happen. Within a couple of months her skin completely cleared up. It has been amazing and life changing. She can walk with confidence and not hide behind makeup that only highlights blemishes. Playing sports have always been an issue as sweat would just aggravate the situation, but now never an issue. Because of the success she has seen using it, I started using the cleansing and facial serum myself. My skin looks and feels great! The facial cleanser has just the right amount of scrub in it not to feel gritty and rough on my skin, yet cleans it so well. The facial serum has been the perfect product for my fine lines and wrinkles. I've noticed a big difference as my makeup doesn't get stuck in deep wrinkle lines anymore and goes on smoother. I highly recommend this product for anyone from a teen struggling with constant blemishes and redness or occasional breakouts to adults like myself looking to better their daily routine for younger looking skin."

Comparative Example 3

Figure 6A:
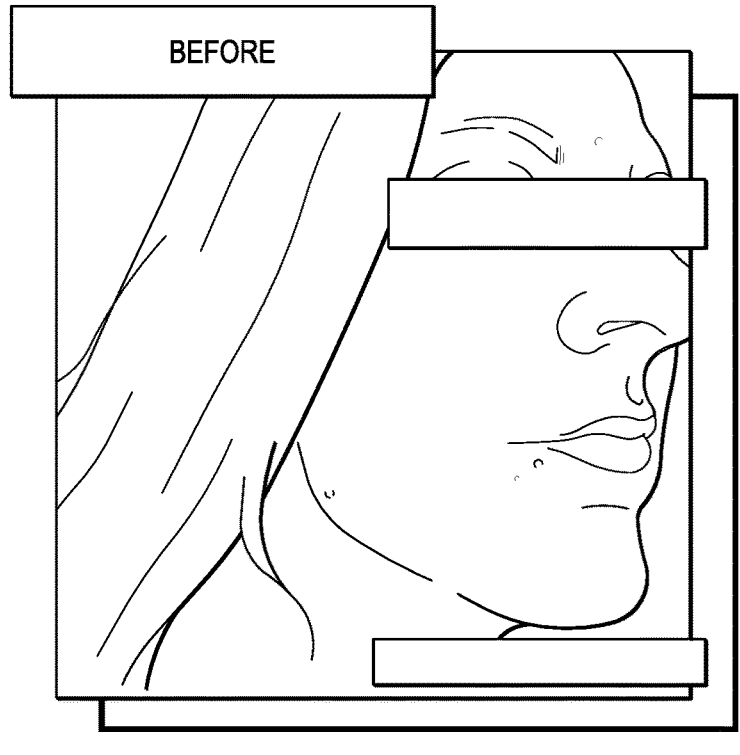
FIGS. 6A and 6B show a comparative example of the present invention versus existing industry standard treatment.
Figure 6B:
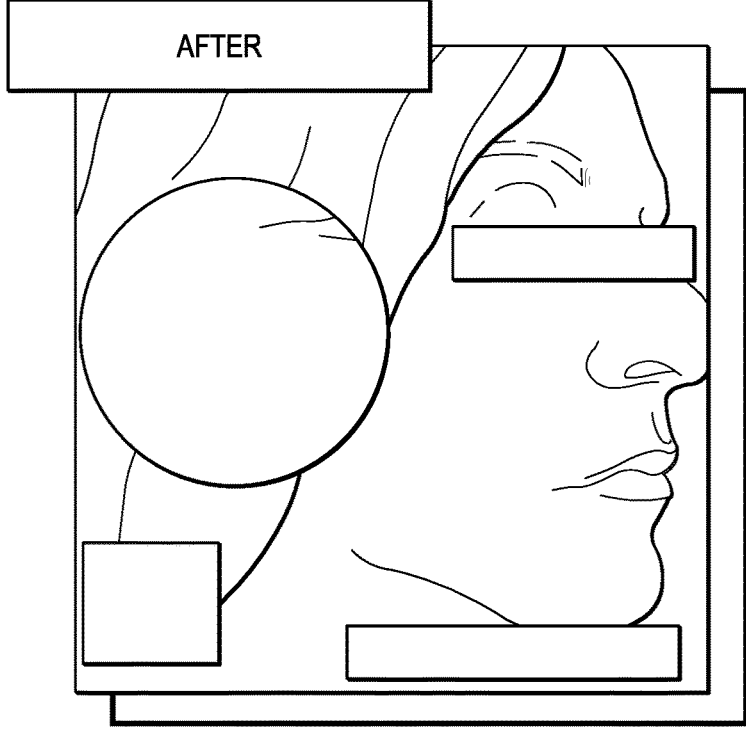

A female subject with a history of acne and skin blemishes, was treated with the composition of the present invention. Previously, the subject had been using for the past 15 years, a composition that included benzoyl peroxide and salicylic acid, widely used in the industry. The comparative composition includes a three-step anti-acne kit that includes a cleanser, a toner and a lotion. Each of the composition previously used by the subject included active agents such as benzoyl peroxide and salicylic acid. In this example the composition used by the subject included 0.5 wt % to about 10 wt % of black willow bark extract, from about 0.2 wt % to about 7 wt % of cat's claw extract, and from about 0.2 wt % to about 8 wt % of dragon's blood extract. FIG. 6A is a before photograph following 3 years of treatment with the prior art three-step anti-acne kit consisting of a cleanser, toner and lotion (benzoyl peroxide and salicylic acid). By comparison, FIG. 6B is a photograph and after just 3 days of treatment with the present invention. FIG. 6A clearly shows widespread acne and other blemishes across the cheek area. FIG. 56B shows the complete resolution of the acne and other blemishes across the entire facila area shown in FIG. 6A. FIG. 6B further includes an inset that shows a close-up view that clearly shows the almost complete resolution of the acne and other blemishes after just 3 days.

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a barrier container, a package, a compartment, or other types of containers such as injection or blow-molded plastic containers into which the compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a liquid, a fluid, or a semi-solid. The containers can have pump or squeeze mechanisms. A kit can also include instructions for using the kit and/or compositions. Instructions can include an explanation of how to apply, use, and maintain the compositions.

In one embodiment, the present invention includes a topical skin care composition consists essentially of black willow bark extract, cat's claw extract, and dragon's blood extract. In another embodiment, the present invention includes a topical skin care composition consists of black willow bark extract, cat's claw extract, and dragon's blood extract. In one aspect, the composition comprises from about 0.5 weight percent (wt %) to about 10 wt % of black willow bark extract. In another aspect, the composition comprises from about 0.2 wt % to about 7 wt % of cat's claw extract. In another aspect, the composition comprises from about 0.2 wt % to about 8 wt % of dragon's blood extract. In another aspect, the composition comprises from about 0.5 wt % to about 10 wt % of black willow bark extract and from about 0.2 wt % to about 7 wt % of cat's claw extract. In another aspect, the composition comprises from about 0.5 wt % to about 10 wt % of black willow bark extract and from about 0.2 wt % to about 8 wt % of dragon's blood extract. In another aspect, the composition comprises from about 0.2 wt % to about 7 wt % of cat's claw extract and from about 0.2 wt % to about 8 wt % of dragon's blood extract. In another aspect, the composition comprises from about 0.5 wt % to about 10 wt % of black willow bark extract, from about 0.2 wt % to about 7 wt % of cat's claw extract, and from about 0.2 wt % to about 8 wt % of dragon's blood extract. In another aspect, the composition is an emulsion, a gel, a cream, a lotion, a serum, or a solution. In another aspect, the composition further comprises at least one of: an emulsifier, a moisturizing agent, an essential oil, a sunscreen, a pharmaceutically active agent, a cosmetic ingredient, a triglyceride, a structuring agent, an antioxidant, a preservative, a gum, a polysaccharide, a polymer, a thickening agent, a gelling agent, or a vitamin. In another aspect, the emulsifier is cetearyl olivate or sorbitan olivate. In another aspect, the moisturizing agent is allantoin. In another aspect, the essential oil is *Copaifera officinalis* (balsam copaiba) resin. In another aspect, the composition comprises black willow bark extract, cat's claw extract, dragon's blood extract, cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incamata* (passionfruit) seed oil, *Caryocar brasiliense* fruit oil, tocopherol, phenoxyethanol, ethylhexylglycerin, and water. In another aspect, the composition comprises 0.5 wt % to about 10 wt % of black willow bark extract, from about 0.2 wt % to about 7 wt % of cat's claw extract, and from about 0.2 wt % to about 8 wt % of dragon's blood extract, from about 0.1 wt % to about 5 wt % cetearyl olivate, from about 0.1 wt % to about 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum maritimum* extract, from about 0.1 wt % to about 5 wt % hydrogenated vegetable oil, from about 0.1 wt % to about 5 wt % *Carapa guianensis* (andiroba)seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

In another embodiment, the present invention includes a method of treating a skin condition consists essentially of topically applying a composition comprising black willow bark extract, cat's claw extract, and dragon's blood extract to skin in need thereof, wherein topical application of the composition to skin in need thereof ameliorates a skin condition. In another embodiment, the present invention includes a method of treating a skin condition consists of topically applying a composition comprising black willow bark extract, cat's claw extract, and dragon's blood extract to skin in need thereof, wherein topical application of the composition to skin in need thereof ameliorates a skin condition. In one aspect, the skin condition is selected from the group consisting of dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions. In another aspect, the composition comprises from about 0.5 wt % to about 10 wt % of black willow bark extract. In another aspect, the composition comprises from about 0.2 wt % to about 7 wt % of cat's claw extract. In another aspect, the composition comprises from about 0.2 wt % to about 8 wt % of dragon's blood extract. In another aspect, the composition comprises from about 0.5 wt % to about 10 wt % of black willow bark extract and from about 0.2 wt % to about 7 wt % of cat's claw extract. In another aspect, the composition comprises from about 0.5 wt % to about 10 wt % of black willow bark extract and from about 0.2 wt % to about 8 wt % of dragon's blood extract. In another aspect, the composition comprises from about 0.2 wt % to about 7 wt % of cat's claw extract and from about 0.2 wt % to about 8 wt % of dragon's blood extract. In another aspect, the composition comprises from about 0.5 wt % to about 10 wt % of black willow bark extract, from about 0.2 wt % to about 7 wt % of cat's claw extract, and from about 0.2 wt % to about 8 wt % of dragon's blood extract. In another aspect, the composition is an emulsion, a gel, a cream, a lotion, a serum, or a solution. In another aspect, the method further comprising adding at least one of: an emulsifier, a moisturizing agent, an essential oil, a sunscreen, a pharmaceutically active agent, a cosmetic ingredient, a triglyceride, a structuring agent, an antioxidant, a preservative, a gum, a polysaccharide, a polymer, a thickening agent, a gelling agent, or a vitamin. In another aspect, the emulsifier is cetearyl olivate or sorbitan olivate. In another aspect, the moisturizing agent is allantoin. In another aspect, the essential oil is *Copaifera officinalis* (balsam copaiba) resin. In another aspect, the composition comprises black willow bark extract, cat's claw extract, dragon's blood extract, cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria*

*dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incarnata* (passionfruit) seed oil, *Caryocar brasiliense* fruit oil, tocopherol, phenoxyethanol, ethylhexylglycerin, and water. In another aspect, the composition comprises 0.5 wt % to about 10 wt % of black willow bark extract, from about 0.2 wt % to about 7 wt % of cat's claw extract, and from about 0.2 wt % to about 8 wt % of dragon's blood extract, from about 0.1 wt % to about 5 wt % cetearyl olivate, from about 0.1 wt % to about 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum maritimum* extract, from about 0.1 wt % to about 5 wt % hydrogenated vegetable oil, from about 0.1 wt % to about 5 wt % *Carapa guianensis* (andiroba)seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

In another embodiment, the present invention includes a kit comprising a composition consists essentially of black willow bark extract, cat's claw extract, and dragon's blood extract disposed within a container. In another embodiment, the present invention includes a kit comprising a composition consists of black willow bark extract, cat's claw extract, and dragon's blood extract disposed within a container.

In another embodiment, the present invention includes a topical skin care composition consists essentially of from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil. In another embodiment, the present invention includes a topical skin care composition consists of from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

In another embodiment, the present invention includes a maintenance therapy regime/regimen for inhibiting or treating moderate to severe acne vulgaris consists essentially of: first topically administering to a subject in need of such treatment a therapeutically effective amount of a first topical skin care composition comprising black willow bark extract, cat's claw extract, and dragon's blood extract for a first predetermined period of time of 1 to 14 days; and subsequent to the first predetermined period of time of 1 to 14 days topically applying onto the affected skin area of the subject in need of such treatment, a therapeutically effective amount of a second topical skin care composition comprising balsam copaiba resin, Camu camu fruit extract, andiroba seed oil, acai fruit oil, pequi fruit oil for a second predetermined period of time up to 8 weeks. In one aspect, the topical skin care composition comprises from about 0.5 wt % to about 10 wt % of black willow bark extract, from about 0.2 wt % to about 7 wt % of cat's claw extract, and from about 0.2 wt % to about 8 wt % of dragon's blood extract formulated into an acceptable topical carrier. In another aspect, the fixed-dose combination is applied topically once a day. In another aspect, the acceptable topical carrier comprises an emulsion, a gel, an aqueous gel, a cream, a lotion, a serum, or a solution. In another aspect, the second topical skin care composition comprises from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

In another embodiment, the present invention includes a method of treating a skin condition selected from the group consisting of dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions with a composition consists essentially of about 0.5 wt % to about 10 wt % of black willow bark extract, from about 0.2 wt % to about 7 wt % of cat's claw extract, and from about 0.2 wt % to about 8 wt % of dragon's blood extract formulated into an acceptable topical carrier. In another embodiment, the present invention includes a method of treating a skin condition selected from the group consisting of dry skin, itchy skin, inflamed skin, erythema, sensitive skin, pruritus, blotches, fine lines or wrinkles, sun damaged skin, dermatitis, psoriasis, folliculitis, blemish, rosacea, acne, eczema, sunburns, burned skin, and skin-inflammatory skin conditions with a composition consists of about 0.5 wt % to about 10 wt % of black willow bark extract, from about 0.2 wt % to about 7 wt % of cat's claw extract, and from about 0.2 wt % to about 8 wt % of dragon's blood extract formulated into an acceptable topical carrier.

In another embodiment, the present invention includes an anti-blemish and anti-aging composition consists essentially of 0.5 wt % to about 10 wt % of black willow bark extract, from about 0.2 wt % to about 7 wt % of cat's claw extract, and from about 0.2 wt % to about 8 wt % of dragon's blood extract, 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil. In another embodiment, the present invention includes an anti-blemish and anti-aging composition consists of 0.5 wt % to about 10 wt % of black willow bark extract, from about 0.2 wt % to about 7 wt % of cat's claw extract, and from about 0.2 wt % to about 8 wt % of dragon's blood extract, 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification. For purposes of the present invention the use of the transition phrase "consisting essentially of" encompasses composition that include additional ingredients in the compositions that does not materially affect the multi-beneficial properties of the combination of black willow bark extract, cat's claw extract, and dragon's blood extract. One such instance would be the inclusion of an ingredient that has a detrimental effect (e.g., reducing the efficacy or stability) on any one of the ingredients identified in the combination, or an ingredient that has no effect on the activity of the compositions, such as inert excipients, stabilizers, buffers, thickening agents, preservatives, scents, and the like. When using the transition phrase "consisting of" refers to only the inclusion in the composition of the listed ingredients, namely, black willow bark extract, cat's claw extract, and dragon's blood extract.

It is contemplated that any embodiment discussed in this specification can be implemented with respect to any method or composition of the invention, and vice versa. Furthermore, compositions of the invention can be used to achieve methods of the invention.

The use of the word "a" or "an", when used in conjunction with the term "comprising" in the claims and/or the specification, may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

What is claimed is:

1. A topical skin care composition for treating a skin condition that is resistant to treatment with benzoyl peroxide and salicylic acid treatment, consisting of black willow bark extract, cat's claw extract, and dragon's blood extract, wherein the composition comprises an effective amount of:

about 3% of black willow bark extract;

about 0.45% of cat's claw extract; and about 0.5% of dragon's blood extract;

in a dermatologically acceptable carrier, wherein the effective amount of the composition is sufficient to treat the skin condition selected from skin blemishes and acne, wherein the skin blemishes or acne are reduced or eliminated and is free of benzoyl peroxide.

2. The composition of claim 1, wherein the composition is an emulsion, a gel, a cream, a lotion, a serum, or a solution.

3. The composition of claim 1, wherein the topically acceptable carrier is selected from at least one of: an emulsifier, a moisturizing agent, an essential oil, a sunscreen, a pharmaceutically active agent, a cosmetic ingredient, a triglyceride, a structuring agent, an antioxidant, a preservative, a gum, a polysaccharide, a polymer, a thickening agent, a gelling agent, or a vitamin; and optionally wherein at least one of the emulsifier is cetearyl olivate or sorbitan olivate; the moisturizing agent is allantoin; or the essential oil is *Copaifera officinalis* (balsam copaiba) resin.

4. The composition of claim 1, wherein the dermatologically acceptable carrier consists of cetearyl olivate, sorbitan olivate, *Copaifera officinalis* (balsam copaiba) resin, glycerin, allantoin, caprylic/capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incarnata* (passionfruit) seed oil, *Caryocar brasiliense* fruit oil, tocopherol, phenoxyethanol, ethylhexylglycerin, and water.

5. The composition of claim 1, wherein the composition consists of from about 0.1 wt % to about 5 wt % cetearyl olivate, from 0.1 wt % to 5 wt % sorbitan olivate, from about 0.1 wt % to about 5 wt % *Copaifera officinalis* (balsam copaiba) resin, from about 0.1 wt % to about 3 wt % glycerin, from about 0.1 wt % to about 5 wt % allantoin, from about 0.1 wt % to about 5 wt % caprylic/capric triglyceride, *Tamarindus indica* seed polysaccharide, from about 0.1 wt % to about 4.0 wt % *Myrciaria dubia* (Camu camu) fruit extract, from about 0.1 wt % to about 3 wt % *Crithmum maritimum* extract, from about 0.1 wt % to about 5 wt % hydrogenated vegetable oil, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 3 wt % *Melaleuca alternifolia* (tea tree) leaf oil, from about 0.1 wt % to about 5 wt % *Passiflora incarnata* (passionfruit) seed oil, from about 0.1 wt % to about 5 wt % *Caryocar brasiliense* (pequi) fruit oil, from about 0.1 wt % to about 3 wt % tocopherol, from about 0.1 wt % to about 1.0 wt % phenoxyethanol, from about 0.1 wt % to about 1.0 wt % ethylhexylglycerin, and from about 10 wt % to about 90 wt % water.

6. A kit comprising the composition of claim 1 disposed within a container.

7. A topical skin care composition for treating skin blemishes or acne that are resistant to treatment with a benzoyl peroxide and salicylic acid treatment, comprising about 3% of black willow bark extract; about 0.45% of cat's claw extract; about 0.5% of dragon's blood extract; from about 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil, wherein the skin blemishes or acne are reduced or eliminated and is free of benzoyl peroxide.

8. An anti-blemish and anti-acne composition for treating skin blemishes or acne that are resistant to treatment with a benzoyl peroxide and salicylic acid treatment, consisting essentially of about 3% of black willow bark extract; about 0.45% of cat's claw extract; 0.2 wt % to 8 wt % about 0.5% of dragon's blood extract, 0.1 wt % to about 5 wt % *Copaifera officinalis* (balsam copaiba) resin, from about 0.1 wt % to about 4.0 wt % *Myrciaria dubia* (Camu camu) fruit extract, from about 0.1 wt % to about 5 wt % *Carapa guianensis* (andiroba) seed oil, from about 0.1 wt % to about 3 wt % *Euterpe oleracea* (acai) fruit oil, from about 0.1 wt % to about 5 wt % *Caryocar brasiliense* (pequi) fruit oil, wherein the skin blemishes or acne are synergistically reduced or eliminated and is free of benzoyl peroxide, and does not cause severe irritation of the skin, allergic reactions, and even throat tightness, breathing problems, or swelling of the eyes, face, lips or tongue associated with such allergic reactions.

9. A topical skin care composition for treating for treating skin blemishes or acne that are resistant to treatment with a benzoyl peroxide and salicylic acid treatment, consisting of:

about 3% of black willow bark extract;

about 0.45% of cat's claw extract; and about 0.5% of dragon's blood extract;

cetearyl olivate, sorbitan olivate, *Copaifera officinalis* (balsam copaiba) resin, glycerin, allantoin, caprylic/ capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incarnata* (passionfruit) seed oil, *Caryocar brasiliense* fruit oil, tocopherol, phenoxyethanol, ethylhexylglycerin, and water, wherein an effective amount of the composition is sufficient to reduce or eliminate skin blemishes or acne and is free of benzoyl peroxide, and does not cause severe irritation of the skin, allergic reactions, and even throat tightness, breathing problems, or swelling of the eyes, face, lips or tongue associated with such allergic reactions.

10. A topical skin care composition for treating a skin condition resistant to treatment with a benzoyl peroxide and salicylic acid treatment consisting of:

an effective amount of:

about 3% of black willow bark extract;

about 0.45% of cat's claw extract; and about 0.5% of dragon's blood extract;

cetearyl olivate, sorbitan olivate, *Copaifera officinalis* (balsam copaiba) resin, glycerin, allantoin, caprylic/ capric triglyceride, *Tamarindus indica* seed polysaccharide, *Chondrus crispus* (carrageenan), *Myrciaria dubia* (Camu camu) fruit extract, *Crithmum maritimum* extract, hydrogenated vegetable oil, *Carapa guianensis* seed oil, *Euterpe oleracea* fruit oil, *Melaleuca alternifolia* (tea tree) leaf oil, *Passiflora incarnata* (passionfruit) seed oil, *Caryocar brasiliense* fruit oil, tocopherol, phenoxyethanol, ethylhexylglycerin, and water, wherein the effective amount of the composition is sufficient to treat the skin, and wherein the blemish and acne are reduced or eliminated and is free of benzoyl peroxide, salicylic acid, adapalene, or retinol.

\* \* \* \* \*